(12) United States Patent
Bent et al.

(10) Patent No.: US 11,069,448 B2
(45) Date of Patent: **\*Jul. 20, 2021**

(54) MULTI AGENT CONSENSUS RESOLUTION AND RE-PLANNING

(71) Applicant: INTERNATIONAL BUSINESS MACHINES CORPORATION, Armonk, NY (US)

(72) Inventors: Oliver E. Bent, Nairobi (KE); Sally Simone Fobi Nsutezo, Nairobi (KE); Antoine Nzeyimana, Nairobi (KE); Meenal Pore, Nairobi (KE); Katherine Tryon, Nairobi (KE); Aisha Walcott, Nairobi (KE)

(73) Assignee: International Business Machines Corporation, Armonk, NY (US)

( * ) Notice: Subject to any disclaimer, the term of this patent is extended or adjusted under 35 U.S.C. 154(b) by 206 days.

This patent is subject to a terminal disclaimer.

(21) Appl. No.: 15/859,572

(22) Filed: Dec. 31, 2017

(65) Prior Publication Data

US 2019/0103192 A1 Apr. 4, 2019

Related U.S. Application Data

(63) Continuation of application No. 15/721,048, filed on Sep. 29, 2017.

(51) Int. Cl.
*G16H 80/00* (2018.01)
*G16H 10/60* (2018.01)
(Continued)

(52) U.S. Cl.
CPC ............. *G16H 80/00* (2018.01); *G16H 10/60* (2018.01); *H04L 9/30* (2013.01); *H04L 9/3239* (2013.01);
(Continued)

(58) Field of Classification Search
CPC ........ G16H 80/00; G16H 10/60; G16H 20/10; H04L 9/3239; H04L 9/3247; H04L 9/30;
(Continued)

(56) References Cited

U.S. PATENT DOCUMENTS

| 7,260,480 B1 * | 8/2007 | Brown | G06F 19/324 702/19 |
| 2003/0154110 A1 | 8/2003 | Walter et al. | |

(Continued)

FOREIGN PATENT DOCUMENTS

| WO | WO 2015175722 A1 | 11/2015 | |
| WO | WO-2018037148 A1 * | 3/2018 | ............. G06Q 50/22 |

OTHER PUBLICATIONS

X. Liang, J. Zhao, S. Shetty, J. Liu and D. Li, "Integrating blockchain for data sharing and collaboration in mobile healthcare applications," 2017 IEEE 28th Annual International Symposium on Personal, Indoor, and Mobile Radio Communications (PIMRC), Montreal, QC, Canada, 2017, pp. 1-5 (Year: 2017).*

(Continued)

*Primary Examiner* — Farid Homayounmehr
*Assistant Examiner* — Zhimei Zhu
(74) *Attorney, Agent, or Firm* — Shimon Benjamin; Otterstedt, Wallace & Kammer, LLP

(57) ABSTRACT

Systems and methods are provided for collaborative decision-making in medicine. The systems can employ a distributed record-keeping and verification system to solicit suggested modifications to an initial healthcare regime from interested healthcare workers. The systems can aggregate the suggested modifications and use a consensus algorithm to determine the most appropriate modification.

18 Claims, 8 Drawing Sheets

(51) Int. Cl.
*H04L 9/30* (2006.01)
*H04L 9/32* (2006.01)
*H04L 9/06* (2006.01)
*G16H 20/10* (2018.01)

(52) U.S. Cl.
CPC .......... *H04L 9/3247* (2013.01); *G16H 20/10* (2018.01); *H04L 9/0643* (2013.01); *H04L 2209/38* (2013.01); *H04L 2209/88* (2013.01)

(58) Field of Classification Search
CPC  H04L 2209/88; H04L 2209/38; H04L 9/0643
See application file for complete search history.

(56) References Cited

U.S. PATENT DOCUMENTS

| | | | |
|---|---|---|---|
| 2006/0271405 A1* | 11/2006 | Cipolle | G06F 19/3456 705/3 |
| 2007/0055552 A1* | 3/2007 | St. Clair | G06F 19/3481 705/3 |
| 2008/0059237 A1* | 3/2008 | Koren | G16H 10/20 705/3 |
| 2009/0076855 A1 | 3/2009 | McCord | |
| 2009/0144200 A1 | 6/2009 | Yoshioka | |
| 2013/0110537 A1* | 5/2013 | Smith | G16H 10/60 705/2 |
| 2015/0032473 A1* | 1/2015 | Sadrieh | G06F 16/73 705/3 |
| 2015/0095987 A1 | 4/2015 | Potash | |
| 2015/0178465 A1* | 6/2015 | Knowlton | G06F 19/3456 705/3 |
| 2015/0244690 A1 | 8/2015 | Mossbarger | |
| 2015/0332283 A1* | 11/2015 | Witchey | G06F 21/00 705/3 |
| 2016/0117471 A1* | 4/2016 | Belt | G06F 19/3456 705/2 |
| 2016/0184497 A1* | 6/2016 | Phillips | A61M 1/0029 604/318 |
| 2016/0300234 A1 | 10/2016 | Moss-Pultz et al. | |
| 2017/0181645 A1 | 6/2017 | Mahalingam et al. | |
| 2017/0372029 A1* | 12/2017 | Saliman | G16H 10/20 |
| 2018/0075558 A1 | 3/2018 | Hill, Sr. et al. | |
| 2018/0117446 A1 | 5/2018 | Tran | |
| 2018/0117447 A1 | 5/2018 | Tran et al. | |
| 2018/0130050 A1 | 5/2018 | Taylor et al. | |
| 2018/0211059 A1* | 7/2018 | Aunger | G06F 21/6263 |
| 2018/0261307 A1* | 9/2018 | Couse | G16H 10/60 |
| 2018/0301051 A1* | 10/2018 | Isozu | G16H 10/00 |
| 2018/0301210 A1* | 10/2018 | Hoff | G16H 20/10 |
| 2019/0057774 A1* | 2/2019 | Velez | G06N 20/00 |
| 2019/0065681 A1* | 2/2019 | Gmeiner | G06F 19/321 |
| 2019/0065763 A1* | 2/2019 | Berg | G16H 30/20 |
| 2019/0108898 A1* | 4/2019 | Gulati | G16H 10/60 |
| 2019/0258672 A1* | 8/2019 | Sadrieh | G06F 16/73 |
| 2019/0279750 A1* | 9/2019 | Wang | G16H 10/60 |
| 2019/0320898 A1* | 10/2019 | Dirghangi | A61B 3/15 |
| 2019/0355483 A1* | 11/2019 | Smurro | G06N 3/04 |
| 2019/0371457 A1* | 12/2019 | Paffel | G06F 16/27 |

OTHER PUBLICATIONS

"Blockchain: Opportunities for health care, A new model for health information exchanges", Jun. 6, 2017, obtained online from <https://web.archive.org/web/20170606114413/https://www2.deloitte.com/us/en/pages/public-sector/articles/blockchain-opportunities-for-health-care.html>, retrieved on Mar. 9, 2021 (Year: 2017).*

Blondel, Vincent D., et al., "On Krause's multi-agent consensus model with state-dependent connectivity." IEEE transactions on Automatic Control 54.11 (2009): 2586-2597, reprinted as pp. 1-15.

Zhirong Qiu et al., "Distributed constrained optimal consensus of multi-agent systems," Automatica, Jun. 30, 2016; vol. 68 pp. 209-215.

Likhachev, M., et al., "Anytime Dynamic A*: An Anytime, Replanning Algorithm," In ICAPS (pp. 262-271 reprinted as pp. 1-10)(Jun. 2005).

Cachin, Christian, "Architecture of the Hyperledger blockchain fabric," In Workshop on Distributed Cryptocurrencies and Consensus Ledgers, Jul. 2016, pp. 1-4.

Oliver E. Bent et al., unpublished U.S. Appl. No. 15/721,048, filed Sep. 29, 2017, Multi Agent Consensus Resolution & Re-Planning, pp. 1-49 plus 8 sheets of drawings.

Paul J. Otterstedt, List of IBM Patents or Patent Applications Treated as Related, Jun. 27, 2018, pp. 1-2.

* cited by examiner

MULTI AGENT CONSENSUS RESOLUTION AND RE-PLANNING

CROSS-REFERENCE TO RELATED APPLICATIONS

This application is a continuation of U.S. patent application Ser. No. 15/721,048 filed Sep. 29, 2017, the complete disclosure of which is expressly incorporated herein by reference in its entirety for all purposes.

BACKGROUND

In embodiments, the technical field of the invention is methods and systems for collaborative decision-making in medicine.

In the field of modern medicine, most interactions involve at least three entities—the patient, the health worker, and an electronic medical records platform. A goal of the patient is to obtain a medical service or medical advice from the health worker in order to appropriately address a current medical problem, or to avoid a potential medical problem. A goal of the health worker is to accurately understand the needs of the patient, and to appropriately address those needs with a service or advice. The platform is present, in part, to provide a medical history of the patient to the health worker, and to ensure that records of the interaction are maintained for future reference. Often, an interaction between patient and health worker results in determination of a treatment regime that is entered into the platform for digital storage and communication.

The determination of a treatment regime is not, however, the end of the process. In many cases the patient may wish to obtain a second opinion, or the health worker may wish to obtain input from other health workers on the contextualized appropriateness of the prescribed regime. Such review of the originally prescribed treatment regime is often desirable, from a policy perspective, because it may result in an improved treatment regime and will also serve to spread information within the medical community. In resource-constrained regions (e.g., parts of the developing world, etc.), however, many challenges are present that inhibits this process. For example, seeking $2^{nd}$ medical opinions in resource-constrained regions is prohibitive due to high cost, low diversity in skills among local health professionals, and a lack of suitable communications with non-local expertise. In addition to the challenges, health workers with only basic medical knowledge and training (such as may be found in resource-constrained regions) often need more advanced support (e.g., doctor- and specialist-level assistance) on prescribing and refining treatment regimes due to lack of in depth knowledge in treating disease and other medical issues. Finally, a lack of efficient medical records keeping and tracking of health worker interventions may hinder the achievements of these goals, especially in resource-constrained regions.

For at least the above reasons, an improved system for obtaining input and consensus on medical treatment regimes is desirable.

SUMMARY

In aspects, the invention is a system to seek and revise medical opinions on a given health case. The system records and manages feedback from health workers. The system crawls medical journals and/or existing guidelines and extracts information pertinent to the case. The system identifies suitable medical doctors on the network to flag for a 2nd opinion. Doctor choice is determined by:
Patient Preferences (e.g., Doctors in a patient's network); Area of expertise; Experience (e.g., number of years practicing and seniority in field); and efficacy: (e.g., doctor's previous success rate in achieving goal through recommendations e.g. hypertension management). The system aggregates $2^{nd}$ opinions and resolves the responses and takes an amelioration action (e.g. proposing a new medication regime).

In an aspect is a method and system for resolving disagreement among experts for a medication regime, allowing consensus resolution and re-planning of the medication regime. The method involves optimizing doctors' consensus on a medication regime.

In an aspect is a method of optimizing a healthcare regime, the method comprising: receiving, by a first user device, a healthcare regime comprising a set of healthcare tokens representative of a set of proposed healthcare actions pertaining to a healthcare user, the proposed healthcare actions proposed by an authoring healthcare worker; obtaining, by the first user device, a digital signature of the authoring healthcare worker; obtaining, by the first user device, a historical block identifier from a healthcare blockchain, the healthcare blockchain representative of healthcare actions taken with respect to the healthcare user, wherein the first user device is one of a plurality of networked devices, each device in the plurality of networked devices maintaining an identical copy of the healthcare blockchain; calculating, by the first user device, a healthcare regime block for the healthcare regime as a function of one or more of the following parameters: the set of healthcare tokens, the digital signature, and the historical block identifier; causing the healthcare blockchain to be updated with the healthcare regime block; receiving, by an user device selected from the first user device and a second user device, at least one proposed modified healthcare token, the at least one proposed modified healthcare token representing at least one modified proposed healthcare action pertaining to the healthcare regime; obtaining, by the user device, a digital signature of an authorized healthcare worker responsible for the at least one proposed modified healthcare action; determining a preference factor for the at least one proposed modified healthcare action; calculating, by the user device, a modified healthcare regime block for the healthcare regime as a function of one or more of the following parameters: the at least one proposed modified healthcare token, the digital signature of the authorized healthcare worker, and the preference factor; causing the healthcare blockchain to be updated with the modified healthcare regime block; and automatically generating a message comprising a healthcare action based on the healthcare blockchain, and transmitting the message via a distributed network to a user account associated with the authoring healthcare worker, wherein the message alters a user interface to display the healthcare action. In embodiments:

causing the healthcare blockchain to be updated with the healthcare regime block comprises transmitting via a distributed network the healthcare regime block to the plurality of networked devices;

the healthcare regime block for the healthcare regime is a function of at least the parameters mentioned above (i.e., the set of healthcare tokens, the digital signature, and the historical block identifier);

the modified healthcare regime block for the healthcare regime is calculated as a function of at least the parameters mentioned above (i.e., the at least one proposed modified healthcare token, the digital signature of the authorized healthcare worker, and the preference factor);

further comprising receiving a plurality of proposed modified healthcare tokens, the plurality of proposed modified healthcare tokens representing a plurality of modified proposed healthcare actions pertaining to the healthcare regime;

further comprising: receiving a plurality of proposed modified healthcare tokens, the plurality of proposed modified healthcare tokens representing a plurality of modified proposed healthcare actions pertaining to the healthcare regime; calculating a plurality of modified healthcare regime blocks for the healthcare regime, one modified healthcare regime block for each of the plurality of proposed modified healthcare tokens received; and causing the healthcare blockchain to be updated with the plurality of modified healthcare regime blocks;

further comprising applying a consensus algorithm to select a most effective modified healthcare regime block from the plurality of modified healthcare regime blocks;

further comprising automatically generating a message comprising a prescription for a medication, the medication based on the selected most effective modified healthcare regime block, and transmitting the message to a user account associated with the authoring healthcare worker for approval by the authoring healthcare worker, wherein approval by the authoring healthcare worker automatically transmits the prescription to a prescription filling system;

further comprising automatically generating a message comprising a healthcare action based on the selected most effective modified healthcare regime block, and transmitting the message via a distributed network to a patient account associated with the healthcare user;

further comprising obtaining an consensus token indicative of an optimization of the healthcare actions and based on the set of healthcare tokens;

wherein the preference factor comprises an experience factor, the experience factor calculated as a function of at least one of the following parameters: an experience of the authorized healthcare worker, an area of expertise of the authorized healthcare worker, and a success rate of the authorized healthcare worker;

the preference factor comprises a compliance factor calculated from aggregated historical patient compliance data pertaining to the at least one proposed modified healthcare action;

the healthcare blockchain further comprises a public key associated with the authoring healthcare worker, the public key operative to enable each device in the plurality of networked devices to check the authenticity of the healthcare regime block;

the healthcare blockchain further comprises a public key associated with the authorized healthcare worker, the public key operative to enable each device in the plurality of networked devices to check the authenticity of the modified healthcare regime block;

causing the healthcare blockchain to be updated with the healthcare regime block comprises transmitting via a distributed network the healthcare regime block to the plurality of networked devices, and wherein the plurality of networked devices are suitable for use by a plurality of authorized healthcare workers;

the generated message comprising a healthcare action is automatically transmitted to the user account associated with the authoring healthcare worker upon generation of a threshold of modified healthcare regime blocks within the healthcare blockchain;

the altering of a user interface to display the healthcare action occurs automatically when a user device associated with the authoring healthcare worker receives the generated message comprising a healthcare action, and wherein the altering includes one or more actions automatically implemented, the one or more actions selected from: display of a visual alert in a GUI; production of an audible alert; modification of a screen view in a GUI; modification of a menu in a GUI; and modification of text in a healthcare user file; and the preference factor comprises aggregated historical patient efficacy data pertaining to the at least one proposed modified healthcare action.

In an aspect is a system for optimizing a healthcare regime, the system comprising one or more computers of a plurality of computers coupled to a network, the one or more computers comprising one or more computer processors coupled to a memory, the memory comprising instructions executable by the one or more computer processors to at least: receive healthcare regime tokens corresponding to a set of proposed healthcare actions, the set of proposed healthcare actions corresponding to a healthcare user associated with a healthcare blockchain; receive a digital signature of an authoring healthcare worker, the authoring healthcare worker responsible for the plurality of proposed healthcare actions; generate a first healthcare regime block comprising one or more of the set of proposed healthcare actions, the digital signature, and a hash of at least a portion of a most recent block of the healthcare blockchain; and transmit the first healthcare regime block to one or more other computers of the plurality of computers on the network, wherein the one or more other computers of the plurality of computers on the network is configured to determine acceptance of the first healthcare regime block and to append the first healthcare regime block to the healthcare blockchain of the healthcare user. In embodiments:

the instructions are executable by the one or more computer processors to: receive healthcare regime tokens corresponding to a set of proposed modified healthcare actions, the set of proposed modified healthcare actions corresponding to the healthcare user; receive a digital signature of an authorized healthcare worker, the authorized healthcare worker responsible for the set of proposed modified healthcare actions; generate a second healthcare regime block comprising one or more of the set of proposed modified healthcare actions, the digital signature of the authorized healthcare worker, and a hash of at least a portion of a most recent block of the healthcare blockchain; and transmit the second healthcare regime block to one or more other computers of the plurality of computers on the network, wherein the one or more other computers of the plurality of computers on the network is configured to determine acceptance of the second healthcare regime block and to append the second healthcare regime block to the healthcare blockchain of the healthcare user;

the instructions are executable by the one or more computer processors to compare the first healthcare regime block against the second healthcare regime block and determine a preference factor for the second healthcare regime block;

the instructions are executable by the one or more computer processors to compare the first healthcare regime block against the second healthcare regime block and determine a preference factor for the second healthcare regime block, wherein the comparison accounts for one or more of the following parameters: an experience of the authorized healthcare worker, an area of expertise of the authorized healthcare worker, and a success rate of the authorized healthcare worker;

the instructions are executable by the one or more computer processors to: receive at least two proposed modified healthcare actions corresponding to the healthcare user; receive at least two digital signatures corresponding to at least two authorized healthcare workers, the at least two authorized healthcare workers responsible for the at least two proposed modified healthcare actions; generate at least two healthcare regime blocks, each of the at least two healthcare regime blocks corresponding to one of the at least two proposed modified healthcare actions; updating the healthcare blockchain with the at least two healthcare regime blocks; compare the at least two healthcare regime blocks to determine a preference factor, wherein the preference factor indicates a preferable block of the at least two healthcare regime blocks; and communicate a message to a user account associated with the authoring healthcare worker, the message comprising the preference factor and the preferable block; and the message further comprises instructions configured to: automatically initiate a prescription medication filling system; automatically initiate a medical device ordering system; or automatically modify a user device associated with the healthcare user to implement a healthcare action with a corresponding treatment schedule.

In an aspect is a method for maintaining healthcare records, the method comprising: maintaining a secure chain of healthcare blocks at a given computing node, wherein the given computing node is part of a set of computing nodes in a distributed network of computing nodes wherein each of the set of computing nodes maintains the secure chain of healthcare blocks, wherein the secure chain of healthcare blocks maintained at each computing node comprises one or more healthcare blocks that respectively represent one or more healthcare actions associated with a healthcare user, and wherein at least one of the healthcare blocks in the secure chain of healthcare blocks represents at least one healthcare action generated by an authoring healthcare worker associated with the healthcare user; adding at least one healthcare block to the secure chain of healthcare blocks maintained at the given computing node in response to receiving a proposed modified healthcare action; determining a preference factor for the proposed modified healthcare action; transmitting a message comprising the preference factor and the proposed modified healthcare action to a user account associated with the authoring healthcare worker; and wherein the maintaining, adding, and determining steps are implemented via at least one processor operatively coupled to a memory associated with the given computing node. In embodiments:

the message is configured to alter a user interface to automatically display the proposed modified healthcare action; and the proposed modified healthcare action is received from an authorized healthcare worker, and wherein the preference factor is determined based on one or more of the following parameters: an experience of the authorized healthcare worker, an area of expertise of the authorized healthcare worker, and a success rate of the authorized healthcare worker (or on all such factors, or any combination thereof).

In an aspect is a method of optimizing a healthcare regime, the method comprising: receiving a healthcare regime comprising a set of healthcare tokens representative of a set of proposed healthcare actions pertaining to a healthcare user, the proposed healthcare actions proposed by an authoring healthcare worker; obtaining a digital signature of the authoring healthcare worker; obtaining a historical block identifier from a healthcare blockchain, the healthcare blockchain representative of healthcare actions taken with respect to the healthcare user; calculating a healthcare regime block for the healthcare regime as a function of one or more of the following parameters: the set of healthcare tokens, the digital signature, and the historical block identifier; causing the healthcare blockchain to be updated with the healthcare regime block; receiving at least one proposed modified healthcare token, the at least one proposed modified healthcare token representing at least one modified proposed healthcare action pertaining to the healthcare regime; obtaining a digital signature of an authorized healthcare worker responsible for the at least one proposed modified healthcare action; determining a preference factor for the at least one proposed modified healthcare action; calculating a modified healthcare regime block for the healthcare regime as a function of one or more of the following parameters: the at least one proposed modified healthcare token, the digital signature of the authorized healthcare worker, and the preference factor; causing the healthcare blockchain to be updated with the modified healthcare regime block; and automatically generating a message comprising a healthcare action based on the healthcare blockchain, and transmitting the message via a distributed network to a user account associated with the authoring healthcare worker, wherein the message alters a user interface to display the healthcare action. Each of the steps above may be carried out from/by appropriate devices independently selected from user devices, central servers, and the like.

These and other aspects of the invention will be apparent to one of skill in the art from the description provided herein, including the examples and claims.

DETAILED DESCRIPTION

Figure 1:
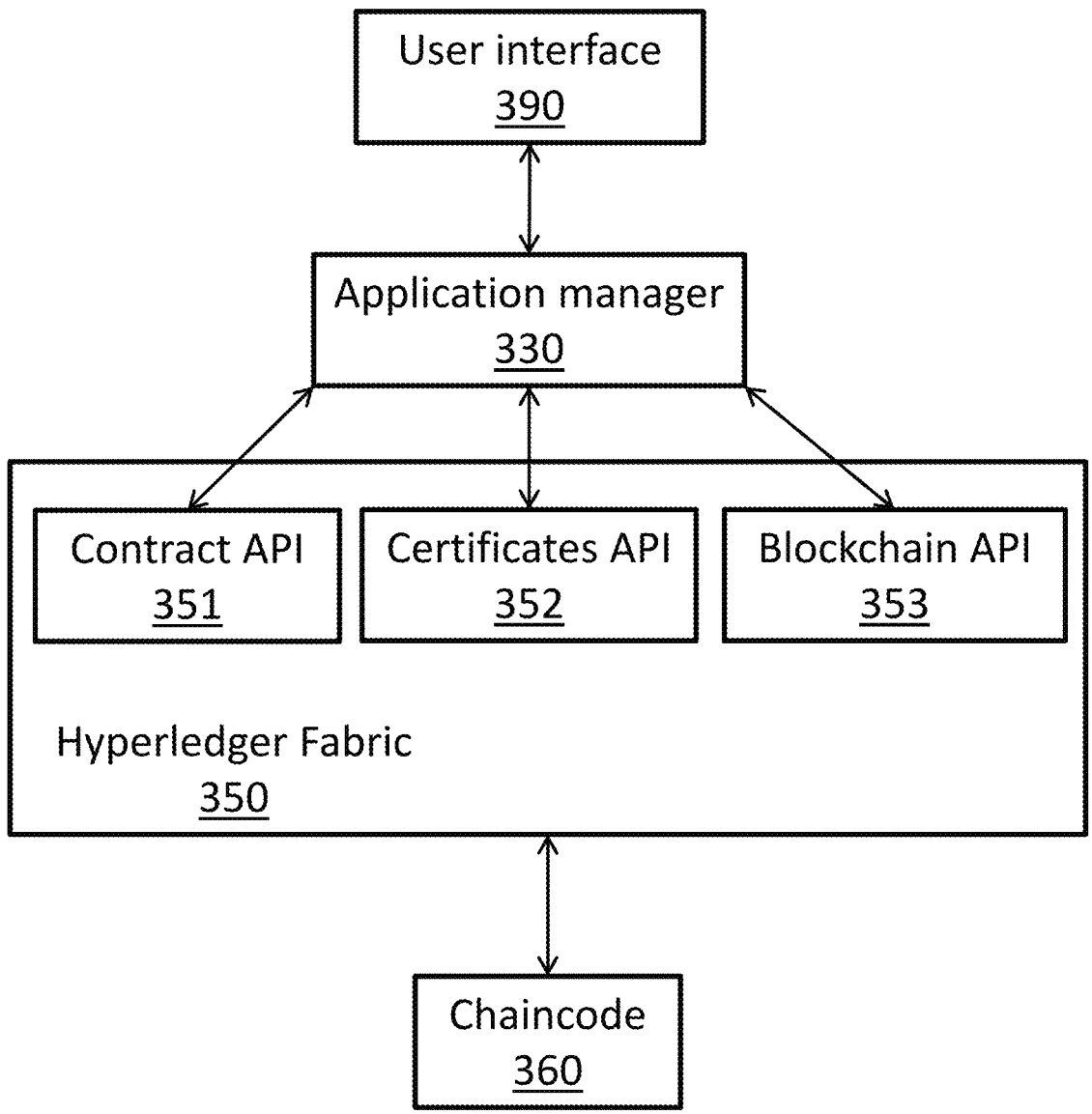
FIG. 1 provides a schematic for a system including an interface according to an embodiment of the invention.

In aspects are devices configured to carry out the methods described herein. The devices may comprise a processor and a memory coupled to the processor, the memory configured to store program instructions for instructing the processor to carry out the method. Further details are provided herein. It will be appreciated, however, that certain components of such devices, and further certain steps of the associated methods, may be omitted from this disclosure for the sake of brevity. The omitted components and steps, however, are merely those that are routinely used in the art and would be easily determined and implemented by those of ordinary skill in the art using nothing more than routine experimentation, the general state of the art, and the disclosure herein. Throughout this specification, where hardware is described, it will be assumed that the devices and methods employing such hardware are suitably equipped with necessary software (including any firmware) to ensure that the devices/methods are fit for the described purpose. Where a function of a device is mentioned, it will be assumed that suitable hardware/software is present to enable the device to operate in such a function (e.g., where a device is in communication with a distributed network, the device comprises a communications module enabling the device to carry out such communications).

In an aspect is a method of optimizing a healthcare regime. Throughout this disclosure, a healthcare "regime" refers to a method of treating a patient wherein the patient suffers from a medical condition and is in need of treatment, or is likely to suffer from a medical condition, or is seeking prophylactic treatment, or is prescribed any of such treatments on recommendation by a health worker. Throughout this disclosure, the term "healthcare worker" is used to describe a variety of workers with an ability to prescribe a healthcare regime. Since a healthcare regime may or may not involve a prescription drug, and since different locations may classify medications differently (e.g., as over the counter or as prescription only), a healthcare worker may or may not be certified for prescribing medications. Furthermore a healthcare worker may be trained in Western-style medicine or any other branch of medicine, including homeopathy and other styles of medicine. Examples of healthcare workers include doctors, nurses (e.g., registered nurses, nurse practitioners, etc.), dentists, psychologists, psychiatrists, homeopathic doctors, doctors of traditional medicine, veterinarians, and the like.

In embodiments the regime may involve administration of a medication (herein also abbreviated "med"). The medication may be of any variety/classification, including prescription or over-the-counter (OTC), generic or brand name, synthetic or naturally occurring, combination drugs, biologic drugs, on-patent or off-patent, vitamins, supplements, analgesics, anti-bacterials, anti-microbials, anti-fungals, anti-retrovirals, or the like. The medication may be intended for administration in combination with other medications, either administered concurrently (co-administered) or separately. The medication may be administered via any appropriate mode, including intravenously, orally, topically, via inhalation, or the like. The medication may be intended for any suitable regimen and dosage, such as hourly, daily, weekly or the like. Many of the above-mentioned factors (dosage, mode of administration, generic v. brand name, etc.) may be the subject of optimization and regime revision described herein.

The regimes described herein are relevant to and intended for a healthcare user. Throughout this disclosure, the "healthcare user" is intended to include any individual or entity desiring, seeking, in need of, deemed in need of, or potentially in need of treatment via a regime as described herein. The user may desire treatment for the purpose of addressing an existing medical condition or for the prophylactic purpose of preventing the development of a future medical condition. Patients in a medical facility or otherwise using a medical resource are examples of healthcare users. The user may be a human or a non-human, examples of the latter including domesticated animals, farm animals, captive non-domesticated animals, and wild animals (i.e., an animal living in the wild or an approximation thereof). The user may be an "entity" such as an automated system for providing treatment regimes for a given diagnosis.

The systems described herein may be deployed anywhere they are needed and appropriate (e.g., compliant with local laws, etc.). In embodiments the systems are particularly suitable for resource-constrained regions (e.g., developing countries, rural areas, or anywhere that access to healthcare technology and expertise is relatively limited or otherwise inadequate). The implementation of a system described herein, typically, requires communication infrastructure such as a cellular (mobile telephony) network, a main electrical grid, etc., although in embodiments one or more of such necessities may be improvised as suitable (e.g., off-grid electricity sources, etc.).

The healthcare regimes described herein are stored digitally in a system according to the disclosure. The system, typically although not necessarily, comprises a plurality of user devices and optionally one or more server(s), all of which are in constant or in regular communication via a distributed network such as a cellular network (e.g., via 3G or some other data-enabled protocol), a physical network such as a local area network, or via some other networking protocol such as Bluetooth, WiFi, or the like. The user device may be a mobile device (e.g., a mobile phone, tablet, laptop, or other mobile device) or a stationary device such as a desktop computer. The user device may be for use by a healthcare user such as a patient, or may be for use by a healthcare worker. The system will be configured so as to know the identity of the user devices on the network, thereby allowing customized communications to be sent to each device. Throughout this disclosure from time to time, it may be stated that a user device performs a calculation, although it will be understood that this language is used for the sake of convenience and is meant to encompass instances where the calculations are actually performed by another device (e.g., an optional server) but that the result is the same. For example, calculation of a new block in a healthcare blockchain may be carried out by a user device, which user device then stores the new block locally, or such calculation may be carried out by a remote server with the resulting block sent back to the user device for local storage on the blockchain.

The systems and methods herein involve the determination of a healthcare regime and its subsequent modification by consensus among healthcare workers. Selected attributes to a healthcare regime are presented below in tabular format. Such data represents a healthcare regime and, in embodiments, a single entry in a database of healthcare regimes.

| Field | Content |
|---|---|
| Unique identifier | |
| Patient identifier | Measurements |
| | Patient history |
| | Current medication(s) |
| | Test results |
| | Diagnosis |
| Medication identifier | Medication/drug |
| | Family |
| | Brand |
| | Generic |
| | Dose |
| | Administration |
| | Frequency |
| Status | Can be modified? |
| | Consensus threshold |
| | Owner identifier |

-continued

| Field | Content |
|---|---|
| Modified Regime 1 | Drug |
| | Family |
| | Brand |
| | Generic |
| | Dose |
| | Administration |
| | Frequency |
| Modified Regime 2 | Drug |
| | Family |
| | Brand |
| | Generic |
| | Dose |
| | Administration |
| | Frequency |

As described herein, the data such as those shown in the table above may be implemented in a database that enables a single patient to contain multiple healthcare regimes, each of which may be the subject of consensus optimization as described. Each of the fields in a database entry for a healthcare regime may be referred to as a healthcare "token" throughout this disclosure. Thus a token may represent a healthcare action such as the identity, classification, dose, regimen, or mode of administration of a medication, proposed for administration to the healthcare user. A suitable database is typically implemented (stored, updated, etc.) on a central server accessible to devices via a distributed network, although other methods of implementation may be suitable. For example, implementation via a cloud computing system architecture or via localized devices may be suitable in some environments.

The database described herein, comprising healthcare regimes for healthcare users, may be implemented, in embodiments, via a blockchain architecture. Such architecture comprises a distributed and encrypted ledger and is created and maintained as described herein, which, along with the general knowledge of blockchain technology, is sufficiently described for an artisan to implement. In embodiments, the blockchain implementation of the database is referred to herein as a healthcare blockchain. The healthcare blockchain comprises one or more healthcare regimes for one or more healthcare users. Further details for the structure of the healthcare blockchain are provided herein.

Selected functions performed by the system and available to a healthcare worker include: create new healthcare regime; view proposed healthcare regimes in his/her network or domain of expertise; propose a modification to a healthcare regime; and invoke consensus resolution on his/her own proposed healthcare regime. These functions may be described in more detail herein, and may be displayed via a user interface for a healthcare worker using a device according to the disclosure. For example a desktop computer may provide a user interface allowing each of these functions. A mobile device such as a tablet or phone may offer a subset of the functions or may offer all of the functions.

A healthcare regime is initially created by a healthcare worker (referred to herein as the authoring healthcare worker) and may be referred to herein as an initial healthcare regime or initial regime. An initial medication regime is a subset of initial healthcare regimes specifically focusing on a medication, although all of the disclosure provided herein pertaining to an initial medication regime is, where the context permits, intended also to be applicable to the broader set of initial healthcare regimes. The initial regime is created on a user device accessible to a healthcare worker, such as a desktop machine in a hospital or doctor's office, or a tablet used by the worker, or the like. The initial regime includes, in embodiments, any combination of the information described in the following paragraphs.

The initial regime may comprise patient information. Such info may include any or all of the following information: the patient's name (where included, this may become a "hidden" field after the initial creation of the regime in order to guarantee patient confidentiality), age, weight, height, BMI, gender, ethnicity, or the like. The patient information may also comprise any or all of the following information pertaining to the patient's prior medical history: prior diagnoses, prior treatment history, family medical history information, known recurring or on-going medical issues, known allergies, or the like.

The initial regime may comprise a list of symptoms (reported by the patient, observed by the medical worker, or a combination thereof) and/or any other information used in the diagnosis by the healthcare worker. Such other information may include one or more laboratory test results (e.g., test results from blood, urine, stool, etc.), one or more radiological scans (e.g., X-ray, CAT scan, MRI scan, etc.), evaluations from specialists or healthcare workers other than the worker creating the initial regime, video files, audio files, image files, or the like.

The initial regime may comprise a status field—this comprises, for example: an identification (name, ID number, or other identifying data) of the healthcare worker responsible for creation of the initial regime (referred to herein as the authoring healthcare worker); the date and location upon/at which the initial regime was created; whether the initial regime may be modified (and the identity or identities of individuals able to modify); and a consensus threshold in a format consistent with the algorithm used in the consensus method and consistent with the disclosure herein.

The initial regime may comprise a medication identifier. The medication identifier includes a variety of information (e.g., selected from: standardized medication name; brand name v generic; manufacturer; medication family; intended dose; suggested mode of administration; suggested frequency/regimen; etc.) about a medication that the authoring healthcare worker intends to prescribe to the healthcare user or otherwise intends to submit to the system described herein for evaluation and possible modification/re-planning.

The initial regime may comprise other information as needed or desired. The system may prompt the authoring healthcare worker to input any or all of the above information (as well as any other mandatory or optional information), e.g., by providing appropriate fields for data entry. An interactive system is also contemplated by the invention, including having visual/audible help tool to assist the authoring healthcare worker with suitable data entry. The system may, in embodiments, assign default values as appropriate or necessary, and may further auto-populate entries based on information obtained from a locally-stored resource or from standard reference Internet sites, or from other resources as appropriate.

The systems and methods may be configured to allow or require that the authoring healthcare worker attach a signature (i.e., a digital signature including a scan of a physical signature) to an initial regime. This allows the system and other users of the system to know the identity of the authoring healthcare worker and also to confirm the validity/authenticity of the initial regime. As described herein, a digital signature may also be used to encrypt data or to otherwise secure data against unauthorized modification, deletion, etc., as well as for verifying identity of users and/or data entered by a user. The digital signature of a healthcare worker may, for example, be stored/generated by the user device allocated to the healthcare worker upon request by that healthcare worker or upon request by the device/system (with approval by the healthcare worker). The systems herein, therefore, are configured to "obtain" a digital signature from a healthcare worker (wherein "obtaining" may involve, e.g., generation of the digital signature with approval by the healthcare worker).

In embodiments, the initial regime, once created, is stored in a healthcare blockchain (also referred to herein, where the context implies, simply as a blockchain) as a collection of healthcare tokens, and such stored information is referred to as a healthcare regime block. The healthcare blockchain is implemented on the systems described herein in order to provide an immutable and distributed record (i.e., a chronicle or ledger, public ledger, private ledger, protected ledger, etc.) of healthcare regimes created and processed as described herein. For a given interaction between a healthcare user and healthcare worker, the initial regime is the first record pertaining to that interaction, and the subsequent actions (e.g., proposed modified healthcare regimes or individual tokens, resolved healthcare regimes, etc.) described herein are added to the healthcare blockchain for that first record. It will be appreciated however that the healthcare blockchain may contain records pertaining to prior interactions between the healthcare worker and the healthcare user, and/or may contain records pertaining to prior interactions between the healthcare user and other healthcare workers.

In embodiments, in order to create/calculate the healthcare regime block, the system uses the set of healthcare tokens, the digital signature of the authoring healthcare worker, and an historical block identifier (or any subset of these, such as the healthcare tokens and the digital signature). The historical block identifier is representative of prior healthcare tokens (e.g., prior actions taken, prior data stored, etc.) pertaining to the healthcare user. The historical block identifier may represent a link to the healthcare user's healthcare blockchain, if one exists. The historical block identifier could comprise a hash value of a previous block header in the healthcare blockchain, possibly the last block added to the healthcare blockchain. As is common in the field of blockchain technologies, the hash value incorporates all previously processed blocks. In such cases the historical block identifier represents a link of continuity across all blocks in the chain. Where a healthcare user is new to the system, a system administrator or a healthcare worker (or an automated process using data input by the user) may create an initial record that thereafter becomes the first historical block identifier, which is subsequently used in generating a healthcare regime block by a healthcare worker. The initial record may comprise any suitable information such as identification information of the healthcare user. In embodiments, the initial record may, itself, be an initial regime.

Once an initial regime is created and stored in the healthcare blockchain as a healthcare regime block, the authoring healthcare worker (or another authorized user) may submit the regime for input from other healthcare workers and, ultimately, for consensus resolution of such input. Alternatively the system may be configured such that any new initial healthcare regime (or selected initial healthcare regimes based on a predetermined criteria) is automatically submitted for consensus resolution. The system may flag the submitted healthcare regime and/or notify other healthcare workers (all workers known to the system, or selected workers based on a predetermined criteria such as area of expertise, location, etc.) that there is a new healthcare regime ready for review and possible revision. Where the system is configured to flag healthcare regimes for consensus review, the system may allow healthcare workers to view all flagged regimes and submit revisions for regimes as desired by the worker.

As with other blockchain architectures, each entry in the blockchain (including an initial regime) is distributed to all devices supporting the blockchain. Each change to the blockchain is also distributed to each of the devices supporting the blockchain, such that each device has a complete version of the blockchain. Abnormalities/discrepancies can be identified where the blockchain records of one device does not match the blockchain records of other devices in the network.

The initial regime (also referred to herein as a first regime, and the entry in the healthcare blockchain referred to herein as the first regime block), once placed in the blockchain, will be subjected to review by healthcare workers other than the authoring healthcare worker. The system may be selective in allowing only specifically authorized (based on any criteria, or based on invitation from the authoring healthcare worker, or invitation of another authorized worker, etc.) healthcare workers to view the initial regime and/or to submit proposed amended regimes. Alternatively, the system may be non-selective, allowing any healthcare worker with access to the healthcare blockchain to view the initial regime and/or to submit proposed amended regimes. In this regard, and as described herein, each healthcare worker granted access to the healthcare blockchain may be given a user account, and that user account includes a field indicating the nature of that access—e.g., the extent to which the worker is granted access to the various records in the blockchain. The worker's user account may also include information about the expertise of the worker, their location, and the like.

An authorized healthcare worker, after reviewing an initial healthcare regime, may decide to submit a proposed modification to the initial healthcare regime. In embodiments, a modification may take the form of a proposed modified healthcare token, or a plurality of proposed modified healthcare tokens. Each modified healthcare token is a token pertaining to the initial healthcare regime (e.g., tokens representing data as described herein, such as data selected from a medication, a medication family, a regimen, a dose, and the like) although in some embodiments the proposed modified healthcare token may be a token that was omitted from the initial healthcare regime (e.g., where the authoring healthcare worker omitted to specify a dosage in the initial healthcare regime, the authorized healthcare worker may submit a healthcare token representing a proposed dosage). Each of the proposed modified healthcare token(s) represents a proposed modified healthcare action pertaining to the initial healthcare regime. In embodiments, the authorized healthcare worker may submit an entire proposed modified healthcare regime, which is stored on the healthcare blockchain and may differ from the initial healthcare regime in every token. This situation is a special case of the submission by the authorized healthcare worker of a modified healthcare set of tokens, inasmuch as the set of tokens is the entire set of tokens that formed the healthcare regime (rather than one token or a subset of tokens). For example, an authorized healthcare worker may determine that every healthcare action proposed by the authoring healthcare worker is non-ideal, and may propose an entirely new regime.

Each modified healthcare token or set of tokens (including an entire substitute healthcare regime) may be referred to herein as a second healthcare regime, and the entry in the blockchain referred to herein as a second healthcare regime block.

The modified healthcare token or set of tokens is the authorized healthcare worker's submission to the blockchain and the systems herein, and represents his/her input with respect to the initial healthcare regime. In order to submit this input, in embodiments the system may require the authorized healthcare worker to append a digital signature thereto, analogous to the signature required of the authoring healthcare worker in creating an initial healthcare regime. In embodiments, the modified healthcare token or set of tokens is used, along with one or more other items, to create a modified healthcare regime block in the healthcare blockchain. The one or more other items that may be so used are selected from, for example: the digital signature of the authorized healthcare worker, a preference factor, and an updated historical block identifier. The digital signature is described above. The updated historical block identifier is determined from the healthcare blockchain and may be, for example and analogously with the historical block identifier, the hash value of the previous block header in the healthcare blockchain, and/or the last block added to the healthcare blockchain. For example, if the authoring healthcare worker is the first to propose a modification to a healthcare regime, the updated historical block identifier may be based on the healthcare regime block.

The preference factor is a factor that is calculated based on a variety of factors such as any one or more of the following: an experience factor personalized to the authorized healthcare worker; a compliance factor pertaining to the modified healthcare token or set of tokens; aggregated historical (and optionally anonymized) patient efficacy data pertaining to the at least one proposed modified healthcare action; and a comparison factor. These are described in more detail below.

In embodiments, the experience factor is calculated as a function of at least one of the following parameters: an experience level of the authorized healthcare worker (i.e., the amount of experience of the worker in the context of the modified healthcare token, such as the number of times the worker has prescribed a specific medication); an area of expertise of the authorized healthcare worker (e.g., whether (or how often) the worker has diagnosed and treated a specific condition, whether the worker has attended specialized courses and programs relevant to a specific condition or related conditions, whether the worker has published in peer-reviewed journals about the specific condition or related conditions and whether such publications have been cited extensively, etc.); colleague ratings of the authorized healthcare worker (e.g., opinion data, survey data, interview data, etc. from other healthcare workers about the healthcare worker); and a success rate of the authorized healthcare worker (e.g., the percentage of patients under the worker's care with the same or relevant condition that improved or were cured within a predetermined period of time, etc.).

In embodiments, the compliance factor is a determined based on a variety of elements pertaining to the extent to which the proposed modified healthcare token(s) complies with medical norms, standardized methods in medicine, legal or regulatory requirements, availability of a suggested treatment (medicine, procedure, etc.) in or near a physical location, and the like. The compliance factor, for example, can be a measure of whether proposed modified healthcare token is legally practicable and/or practically feasible for a healthcare user located in a specific, known location. The compliance factor can also or alternatively be a measure of the extent to which the medical profession has formally (or informally) recognized a treatment as effective for a specific medical condition. For example, the compliance factor can be relatively lower for a treatment that is "off-label" or is considered experimental.

In embodiments, the preference factor is in whole or in part determined by aggregated patient efficacy data. Such data can be anonymized or not anonymized, and can be sourced from publicly available resources or proprietary/confidential, or combinations thereof. Such data can be based on animal models or human trials, or combinations thereof. Such data can be raw data or interpreted data, or combinations thereof. Such data can be specifically for the exact same medical procedure or medication as the proposed modified healthcare token, or can be for a different but relevant procedure or medication (with an appropriate scaling factor, in the case of a different procedure/medication, based on the amount of difference).

In embodiments, the preference factor is a function of a comparison factor that is determined by a comparison of a healthcare token with another healthcare token. The comparison, typically, involves comparing a modified healthcare token with another modified healthcare token or with a healthcare token from the initial regime, provided that the compared tokens pertain to the same or comparable subject matter (e.g., a family of drugs is compared with another family of drugs, or a dosage is compared with another dosage). The preference factor can involve comparison of one set of multiple tokens with another set of multiple tokens, again provided that the two sets of tokens pertain to the same or comparable subject matter (e.g., a dose and regimen, in combination, can be compared with another dose and regimen, in combination). The determined value of the comparison factor can be based on a variety of factors used for evaluating the comparison such as clinical data (or other experimental data, studies, anecdotes, etc.) pertaining to the efficacy of one token compared with another token.

Any or all of the above factors, which may be used to calculate the preference factor of a proposed modification to a healthcare regime, pertain to a specific healthcare token or a combination of tokens, or to an entire initial healthcare regime or an entire proposed modified healthcare regime. The specific token or combination of tokens may be from the initial healthcare regime, or may be from the proposed modification to the healthcare regime. For example, where the proposed modification to the healthcare regime comprises a token that identifies a proposed medication, the experience factor may be based on stored data pertaining to the experience that the authorized healthcare worker has with that specific proposed medication. Also for example, where the initial healthcare regime comprises a diagnosis of a specific medical condition, the experience factor may be based on stored data pertaining to the experience and success rate that the authorized healthcare worker has with treating that medical condition. The stored data just mentioned may be based on data obtained from the healthcare worker and/or may be inferred/obtained from medical records.

In embodiments, the proposed modified healthcare token(s) received from the authorized healthcare worker is/are packaged into a modified healthcare regime block and stored in the blockchain. The system may receive a plurality of modified healthcare regime blocks from a plurality of authorized healthcare workers (e.g., 2, 3, 4, 5, or more than 5 workers). The system may place a limit on the number of modified healthcare regime blocks that are accepted for any given initial regime (e.g., not more than 2, 3, 4, 5, or 10 modified healthcare regime blocks will be accepted), and/or may limit the time allotted for receiving modified healthcare regime blocks (e.g., not more than 1, 2, 3, 5, 7, or 14 days allowed for receipt), and/or may impose any other limitations on receipt of the modified healthcare regime blocks as desired.

As mentioned herein, healthcare workers with access to the system will be given a user account. In embodiments, the user account of the authoring healthcare worker comprises a dashboard function that enables him/her to view the status of their initial regime and request for modified healthcare regimes. Thus, the user's dashboard is automatically updated when an authorized healthcare worker submits a modified healthcare regime block (pertaining to that user's initial regime) to the healthcare blockchain, such that the authoring healthcare worker can readily determine how many modified healthcare regime blocks have been submitted (and, in embodiments, the identities of the submitting authorized healthcare workers).

As mentioned herein, in embodiments each modified healthcare regime block comprises a preference factor. In embodiments, the system, or the authoring healthcare worker, can use the preference factor or any component thereof to determine the most desirable proposed modified healthcare regime for replacing/modifying the initial regime. The system can also use the preference factor or any component thereof to rank the received proposed modified healthcare regimes, and the rankings can be communicated to any user such as the authoring healthcare worker. As described herein, the preference factor may be used directly in the consensus algorithm when evaluating the received proposed modified healthcare regimes, and the preference factor can also be used as a secondary ranking factor in addition or in the alternative to the consensus algorithm.

At any desired time, the authoring healthcare worker can request that the system apply a consensus algorithm to the modified healthcare regime blocks received for an initial regime. In embodiments, the request can alternatively be made by another healthcare worker granted authorization to make such a request. In embodiments, the request can be automatically generated by the system in response to surpassing a predetermined threshold (e.g., a minimum number of received proposed modified healthcare regimes, or a set time limit for receipt). In any of these ways, the system submits the received proposed modified healthcare regimes to a consensus algorithm. The consensus algorithm is any algorithm that takes as input the modified healthcare regime blocks (or, in embodiments, selected tokens from such blocks) as well as the initial regime block and determines a consensus healthcare regime block (or, in embodiments, consensus tokens form such blocks). In embodiments, the system/algorithm may be configured to select tokens from multiple modified healthcare regime blocks (as well as the initial regime block) in order to build a consensus healthcare regime block that is an aggregate of other blocks. Any suitable consensus algorithm(s) now known or later developed may be used. For example, the consensus algorithm may select a consensus block/token based on majority (or highest percentage, or unanimous, etc.) agreement across the various authorized healthcare workers, as determined from the content of the modified healthcare blocks submitted by such workers. Alternatively, the consensus algorithm may select a regime block because the author of the block is the most respected healthcare worker in the relevant field, and/or because the author of the block has a very high success rate of cure with the particular medical condition (e.g., a rate above a threshold, such as greater than or equal to 90, 95, or 99%). The consensus algorithm can be applied to a healthcare regime as a whole, or can be applied to any portion of a healthcare regime, include a specific token within a healthcare regime. For example, where a healthcare regime pertains to treatment of a patient diagnosed with a specific condition, and the initial healthcare regime suggests prescription of a specific medication administered daily by mouth (oral administration) at a specific dosage, the consensus algorithm can be applied to modified healthcare blocks as a whole (which may include therein suggestions for modifying each of the medication, the mode of administration, the dosage, and the regimen) or to any portion of the modified healthcare blocks (e.g., just to the regimen or just to the dosage).

Blockchain Structure

As mentioned herein, the systems and methods involve a healthcare blockchain. As with other databases implemented via blockchain architecture, the healthcare blockchain is a cryptographic, distributed, verifiable, shared, and immutable structure. The entire blockchain structure is maintained on every node within the network implementing the blockchain at all times. Data are encrypted using public/private keys. In addition to the healthcare regime blocks, the healthcare blockchain may also comprise parties (i.e., healthcare workers, healthcare users, etc.), keys used for encryption, and other items as necessary and appropriate. Data stored into the blockchain are hashed (e.g., using a hash function from SHA-2 such as SHA-256).

Blocks in the healthcare blockchain may be encrypted. For example, a private key associated with an authoring healthcare worker may be used to encrypt a healthcare regime block, and a private key associated with an authorized healthcare worker may be used to encrypt a modified healthcare regime block. Other private keys associated with other users storing information on the blockchain may also be used. Public keys corresponding to such users, and operative to check the authenticity of the healthcare regime block or modified healthcare regime block (or other data on the blockchain), may be stored in the healthcare blockchain so that any node in the network can carry out such verification.

In embodiments, the system architecture for implementing the blockchain can be represented with a layered nomenclature. An application layer implements a user interface and allows users (healthcare workers and healthcare users, e.g., plus administrators and other users as appropriate) to interact with the database. The user interface may include a GUI or other user interface as desired, and may be suitable for running on any conceivable device that may be used by a user. The application layer is the most abstracted layer and, typically, the only layer with which the user will interact. On the other hand, the least abstracted layer defines the format/structure of the blockchain, the rules for validating the blockchain, and the protocol for adding new blocks to the ledger. This base layer, referred to herein as a Consensus Layer, may involve a consensus algorithm in order to allow nodes to determine which of multiple candidate blockchain ledgers is authentic (i.e., is the consensus ledger). Between the consensus layer and the application layer, there may be one or more layers (depending on the classification and nomenclature scheme used). For example, an API layer may be present allowing an interface between the application and the implementing nodes—this layer, for example, providing communication and access rules that determine the types of devices that may be used by users. Also for example, a transport layer (also referred to as a propagation layer) may be present defining the communication system between nodes in the distributed ledger. Other components and layer definitions may be used as appropriate for implementing the blockchain.

Output

In embodiments, the output of the consensus algorithm is a consensus healthcare regime block, which consists of the tokens that are selected by the consensus algorithm and comprise a consensus healthcare regime. The consensus healthcare regime may be completely different from the initial healthcare regime, differing in every token, or may differ from the initial healthcare regime by only one or a selection of tokens (e.g., 2, 3, 4, or more than 4 tokens). The consensus healthcare regime block is stored on the blockchain and identified as such therein. In embodiments the consensus algorithm may output a single token or a subset of tokens. In such embodiments the output does not form an entire healthcare regime (i.e., it is more targeted and may simply indicate that the initial healthcare regime is acceptable but for one or a small subset of tokens that are recommended for change). The output token(s) is/are stored on the blockchain as consensus token(s).

The output further comprises, in embodiments, a healthcare action (also referred to herein as a "proposed modified healthcare action") based on the blockchain as modified by inclusion of the consensus healthcare regime block or consensus token(s). Recalling that a healthcare token as described herein may represent a proposed healthcare action, the action then may be precisely the same as a consensus token (e.g., a token indicating dosage, which is self-evident in how to implement with the healthcare user). Alternatively or in addition the action may be a sequence of instructions based on one or more tokens (e.g., administration of a first medication at a specific dosage/regimen followed by administration of a second medication at another specific dosage/regimen) identified by the consensus algorithm. The action may be automatically generated by the system based on the consensus healthcare regime or token.

Once the consensus algorithm has selected a consensus healthcare regime block (or a consensus token), and stored the block (or consensus token) to the blockchain, and generated a healthcare action from such selected consensus information, the system notifies the authoring healthcare worker. The notification can take any suitable form. In embodiments, the notification is via a message generated automatically by the system and delivered via a distributed network (e.g., an SMS, or an email, or some other message system) to the user account (e.g., phone number, email address, etc.) of the authoring healthcare worker. In such embodiments the message may simply indicate the presence in the blockchain of the consensus block or token(s), but not contain any specific information about the consensus information. In embodiments the message may comprise the contents of the consensus block or token(s), such that the authoring healthcare worker immediately receives the consensus information and is not required to login to his/her account on the system to view such information. In embodiments the message is configured to alter a user interface to display the message or a part thereof, including the contents of the message (which may, for privacy purposes, be password protected or otherwise protected against unauthorized viewing).

In embodiments, the message is configured to automatically initiate an action in a system based on the determined consensus information (token(s) or modified healthcare regime block). For example, the message may comprise instructions configured to: automatically initiate a prescription medication filling system; automatically initiate a medical device ordering system; or automatically modify a user device associated with the healthcare user to implement a healthcare action with a corresponding treatment schedule.

In embodiments, and particularly where regulations/laws require a healthcare professional to initiate a medication prescription system to fill a prescription, the output may further comprise automatically generating a message comprising a prescription for a medication, the medication based on the selected most effective modified healthcare regime block, and transmitting the message to a user account associated with the authoring healthcare worker for approval by the authoring healthcare worker, wherein approval by the authoring healthcare worker automatically transmits the prescription to a prescription filling system. Other automated healthcare actions may also be initiated as output of the system, such as scheduling a medical test (e.g., an MRI, a CAT scan, or a blood test), or scheduling an appointment with a specialist healthcare worker.

In embodiments the output further involves automatically generating a message comprising a healthcare action based on the selected most effective modified healthcare regime block, and transmitting the message via a distributed network to a patient account associated with the healthcare user.

In embodiments, an authorized healthcare worker may determine that the proposed initial healthcare regime is dangerous, ineffective, or otherwise unfit for the healthcare user. In such embodiments, the system is configured to allow the authorized healthcare worker to specially flag such critical information, and the system may generate a message configured to automatically display an alert (e.g., a flashing message, an audible tone, or the like) to the authoring healthcare worker. The message may further cause an automated system to enter a "safe" mode in view of the critical information (e.g., a prescription medication filling system can be automatically instructed to refuse to fill a prescription for a medication that may be dangerous to a patient with a given profile).

System

Blockchain architectures and methods of maintaining the architecture and data in a blockchain are known in the art. In embodiments, the systems described herein comprise a plurality of interconnected nodes (i.e., networked devices including user devices) such as personal desktop computers or the like, each of which or a subset of which accessible by authorized healthcare workers and authoring healthcare workers. A central server may be employed (e.g., for storage of data such as a user database, and/or for carrying out resource-intensive computations), or the entire system may be distributed without a central server. The system may include an interface and appropriate networking software/hardware for users to use mobile devices (e.g., cellular phones, tablets, etc.). The system may include software/hardware suitable for adding nodes when desired, wherein each time a node is added, the node is incorporated into the blockchain (e.g., receives a complete copy of the blockchain from one or more other nodes as well as all of the rules and algorithms associated with the blockchain, including consensus algorithms, etc.).

In embodiments, the systems described herein maintain a database of healthcare workers as well as information about each worker—e.g., area of expertise, experience in various areas, trainings, professional accolades and memberships, research activities, affiliations, physical location and physical areas serviced, and the like. Each healthcare worker is given an individual database entry, and the database entry can include all of the above information as well as a status of the healthcare worker (e.g., authorized to submit initial healthcare regimes, authorized to submit modified healthcare regimes in all or selected areas, etc.), an address or other contact information, and the like. The database entry can also include all of the information that is used to determine the experience factor described herein (e.g., the colleague ratings, etc.). The database may be maintained at a central server or, alternatively, also in a distributed manner such as a blockchain architecture. In embodiments, the database of healthcare workers is maintained as data on the healthcare blockchain and is verifiable by all nodes and users of the blockchain. Similarly, the system may include a database of healthcare users (i.e., patients) for which healthcare regime blocks have been (or could be) created on the blockchain. Again, the database can be maintained in the healthcare blockchain or in any other suitable matter. In embodiments, such data includes medical histories and other information about each healthcare user.

The system may involve, in embodiments, sensors that provide sensory input used by the healthcare worker or used directly by the healthcare blockchain. Such sensors may sense a variety of data including medications (e.g., a scanner scanning a barcode), a health status of a healthcare user (e.g., a measurement of the user's vital signs such as temperature, weight, etc.), an observation of the healthcare user's physical or emotional state, or any other data that can be measured by a sensor in the context. The sensor data may be automatically captured by the system or may be manually entered by the healthcare worker. In embodiments, the sensor data is used by an authoring healthcare worker to generate an initial healthcare regime.

Methods

The methods described herein allow a healthcare worker to propose a healthcare regime and then optimize that regime via input from other healthcare workers using a distributed network.

A sample (simplified) workflow includes the following steps: an initial healthcare regime is created by an authoring healthcare worker and the same is sent to the blockchain network to get a consensus second opinion. Multiple healthcare workers (including some experts in the specific condition described in the healthcare regime) on the network propose various modifications to the medication regime, each of which is distributed and stored to the blockchain. The consensus resolution algorithm is invoked to determine the most appropriate modification, which is then communicated to the authoring healthcare worker in the form of information and/or instructions for taking an action. Subsequent re-planning (i.e., revising the initial healthcare regime) is undertaken by the healthcare worker or automatically by the system.

In embodiments the methods involve receiving a set of healthcare tokens representing the healthcare actions of a healthcare regime, obtaining a historical block identifier from a healthcare blockchain, the healthcare blockchain (and the tokens therein) representative of healthcare actions taken with respect to the healthcare user; calculating a healthcare regime block for the healthcare regime as a function of one or more of the following parameters: the set of healthcare tokens, the digital signature, and the historical block identifier (or all of these factors, or any combination thereof); and causing the healthcare blockchain to be updated with the healthcare regime block. The healthcare regime block is then reviewed by other healthcare workers, one (or multiple) of which may submit at least one proposed modified healthcare token, the at least one proposed modified healthcare token representing at least one modified proposed healthcare action pertaining to the healthcare regime. The healthcare worker making such a submission (or the device they are using) submits a digital signature, which is used (along with other data such as a preference factor, the token, etc.) to generate a new block for the healthcare blockchain. The blockchain is then updated. The system may automatically notify the authoring healthcare worker of the addition to the blockchain. The system may also receive a plurality of proposed modified healthcare tokens from a plurality of healthcare workers, and update the blockchain with each proposal. With such a plurality, the system may apply a consensus algorithm to determine the most appropriate proposed modified healthcare token(s). Such determined token is then communicated to the authoring healthcare worker, and may further cause an automated system to issue a prescription, schedule a medical test, or take some other healthcare action.

In embodiments is a method using a system for optimizing a healthcare regime, the system comprising one or more computers of a plurality of computers coupled to a network, the one or more computers comprising one or more computer processors coupled to a memory, the memory comprising instructions executable by the one or more computer processors to carry out any of the methods disclosed herein. For example, the method may involve storing healthcare regimes and proposed modified healthcare regimes in a blockchain architecture. The computers implementing the blockchain are configured to analyse input from healthcare workers and, when such analysis shows an appropriate set of tokens, generate new blocks for the blockchain. The blockchain is then updated on all computers implementing the blockchain. Throughout this disclosure, the term "chaincode" may be used to refer to the machine-readable instructions and data implementing the blockchain on the various computers.

In embodiments is a method for maintaining healthcare records, the method comprising: maintaining a secure chain of healthcare blocks at a given computing node, wherein the given computing node is part of a set of computing nodes in a distributed network of computing nodes wherein each of the set of computing nodes maintains the secure chain of healthcare blocks, wherein the secure chain of healthcare blocks maintained at each computing node comprises one or more healthcare blocks that respectively represent one or more healthcare actions associated with a healthcare user, and wherein at least one of the healthcare blocks in the secure chain of healthcare blocks represents at least one healthcare action generated by an authoring healthcare worker associated with the healthcare user; adding at least one healthcare block to the secure chain of healthcare blocks maintained at the given computing node in response to receiving a proposed modified healthcare action; determining a preference factor for the proposed modified healthcare action; transmitting a message comprising the preference factor and the proposed modified healthcare action to a user account associated with the authoring healthcare worker; wherein the maintaining, adding, and determining steps are implemented via at least one processor operatively coupled to a memory associated with the given computing node.

Various embodiments of the invention are described more fully hereinafter with reference to the accompanying drawings. The invention herein may be embodied in many different forms and should not be construed as limited to the embodiments set forth in the drawings; rather, these embodiments are provided to provide further illustrative non-limiting examples. Arrowheads in the figures are provided merely as examples of directions for the flow of data but are not exhaustive and are not meant to be limiting—i.e., data may flow (where appropriate) in directions that are not shown by arrowheads in the figures. Similar numbers in different figures are meant to refer to similar components.

With reference to FIG. 1, there is shown a (partial) schematic for a system including an interface according to an embodiment of the invention. User interface 390 is operating on a user device (not shown) as described herein, and allows a healthcare worker to interface with the system and, specifically, with the application manager 330 being executed on the user device. Application manager 330 manages the activities of the healthcare blockchain, which is comprised of chaincode 360 executing hyperledger fabric 350. Hyperledger fabric 350 is, in turn, comprised of various application programming interfaces (APIs) including, at least, contract API 351, certificates API 352, and blockchain API 353.

Figure 2:
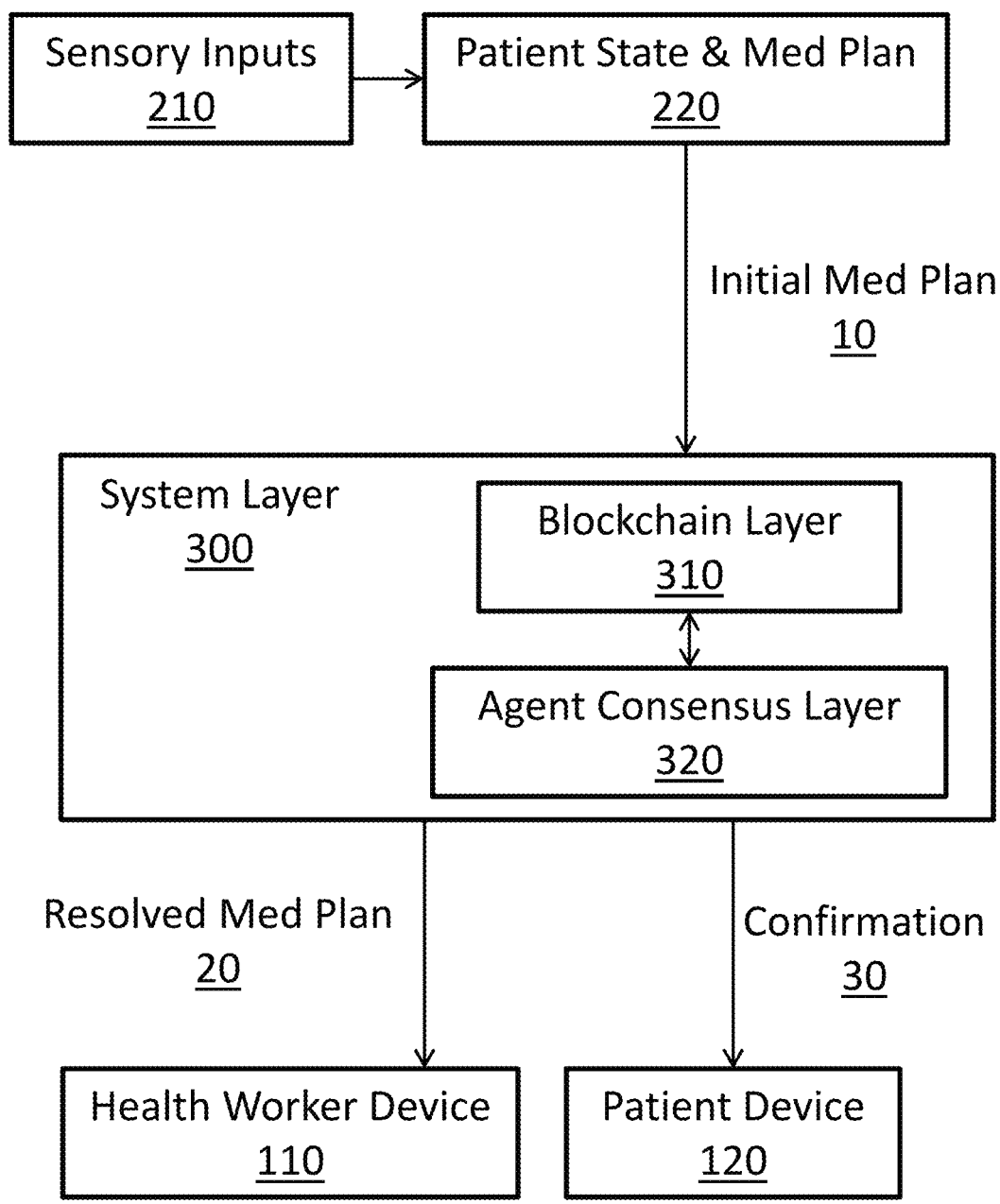
FIG. 2 provides a schematic for an embodiment involving collecting data, processing the data, and transmitting an output according to an embodiment of the invention.

With reference to FIG. 2 there is shown a (partial) schematic for an embodiment involving collecting data, processing the data, and transmitting an output according to an embodiment of the invention. Sensory inputs 210 are generated by sensors (not shown), as described herein. The sensor data are then transferred to the module Patient State & Medication Plan 220, which allows an authoring healthcare worker to generate an Initial Medication Plan 10 (also referred to herein as an initial healthcare regime). The Initial Medication Plan 10 is sent to the system executing the healthcare blockchain. System layer 300 (comprised of Blockchain layer 310 and agent consensus layer 320) receives the Plan 10 and adds it to the blockchain. Confirmation 30 of the addition may be sent to Patient Device 120, in embodiments. Other healthcare workers (not shown) may propose modifications to Plan 10, which are then stored on the blockchain. The system determines a Resolved Medication Plan 20 (also referred to herein as a Consensus Regime), which is sent to Healthcare Worker Device 110.

Figure 3:
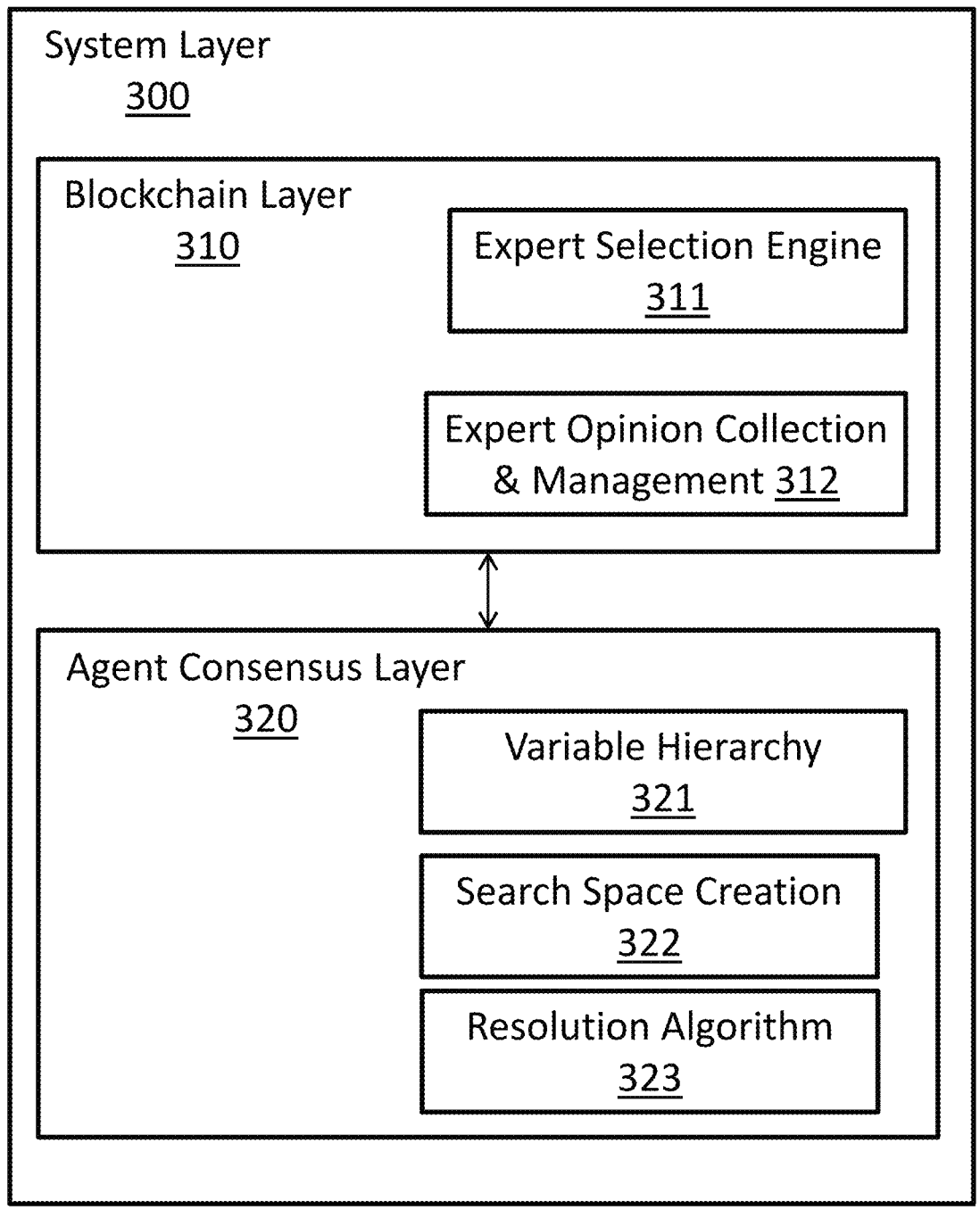
FIG. 3 provides a schematic for an example system layer and the details of components therein according to an embodiment of the invention.

With reference to FIG. 3 there is shown a (partial) schematic for an example system layer and the details of components therein according to an embodiment of the invention. Blockchain layer 310 is comprised of an Expert Selection Engine 311, which uses various factors such as the experience factor or other factors to pre-select healthcare workers to be invited to submit proposed modified healthcare regimes/tokens. Blockchain layer 310 also comprises Expert Opinion Collection & Management Engine 312, which is configured to receive proposed modified healthcare regimes/tokens from healthcare workers. Also part of system layer 300 is Agent Consensus Layer 320, which comprises Variable Hierarchy 321, Search Space Creation module 322, and Resolution Algorithm 323, all of which work together to determine a consensus regime from the various inputs from authoring and authorized healthcare workers.

Figure 4:
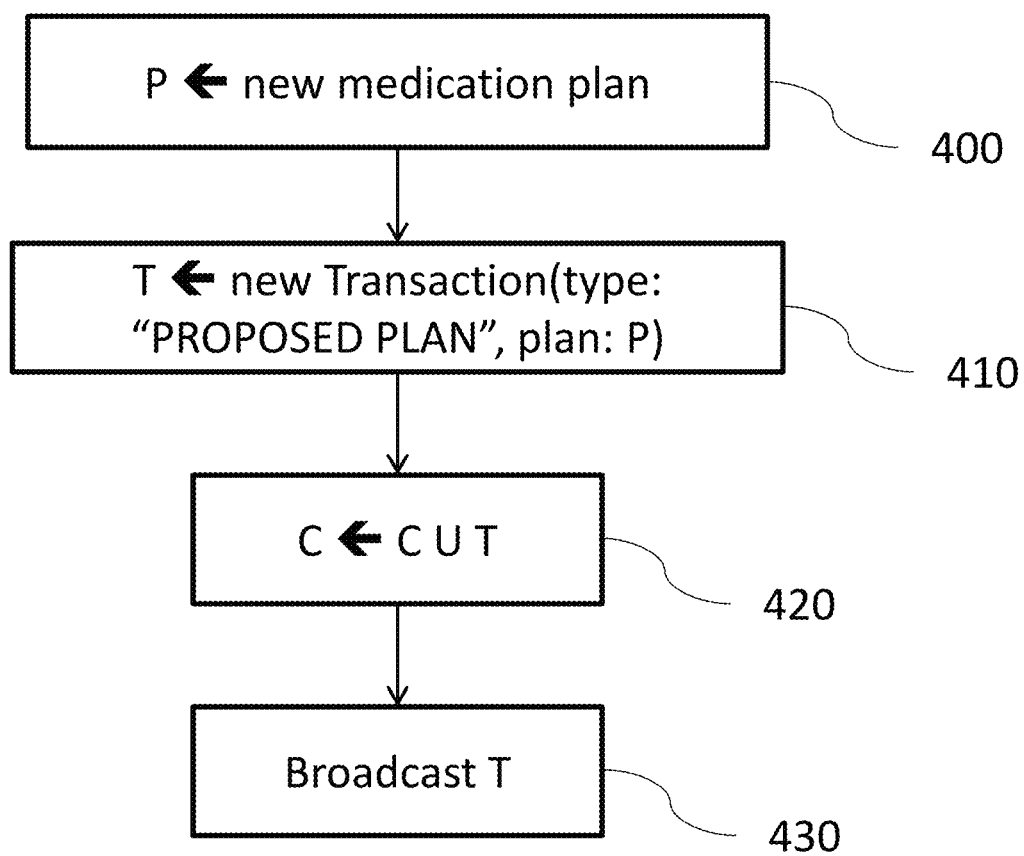
FIGS. 4, 5, and 6 provide a schematic for sample algorithm steps involved in processing a new medication regime, adding transactions to a list of transactions, and creating a new optimal medication regime according to an embodiment of the invention.
Figure 5:
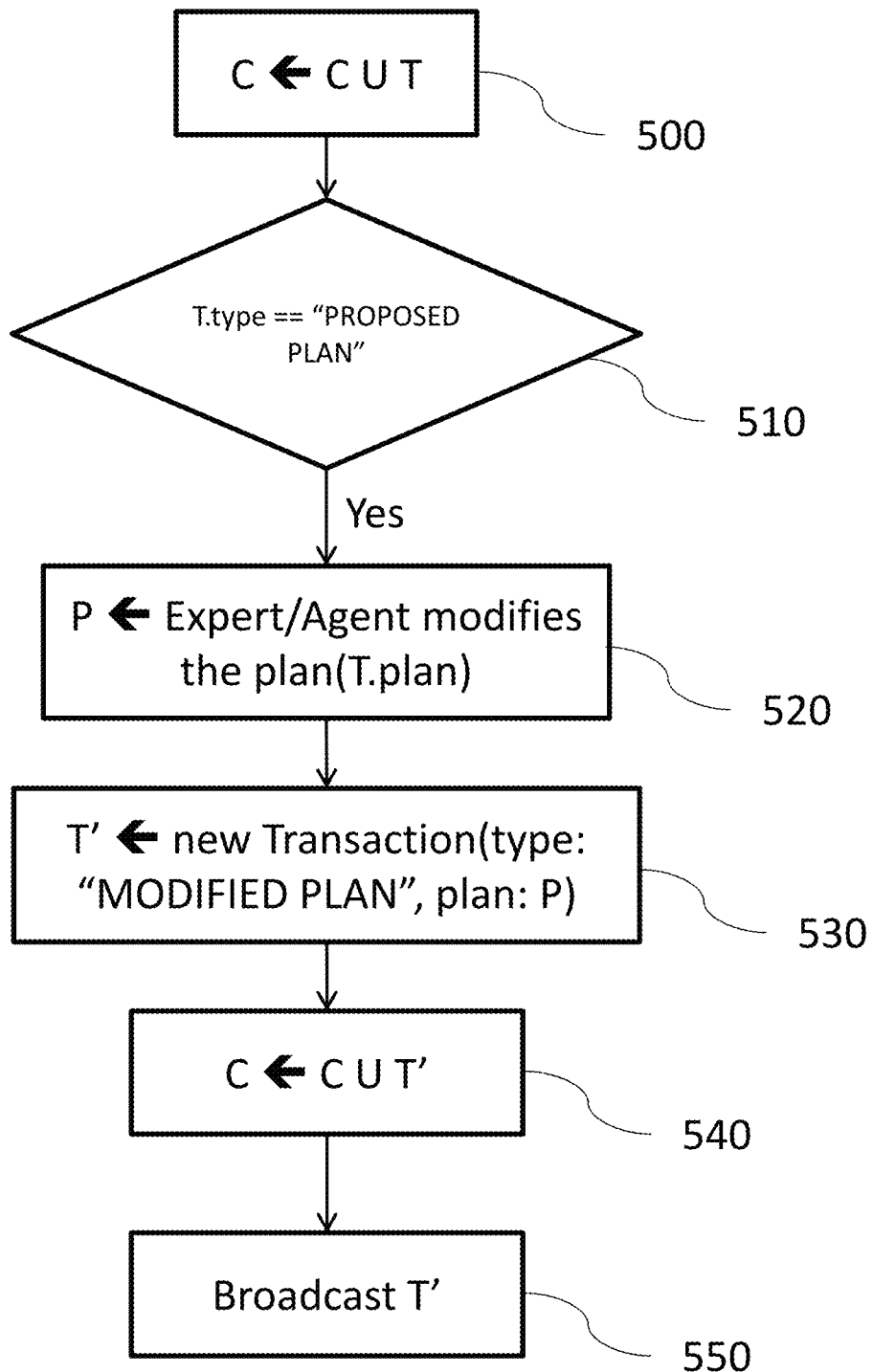
Figure 6:
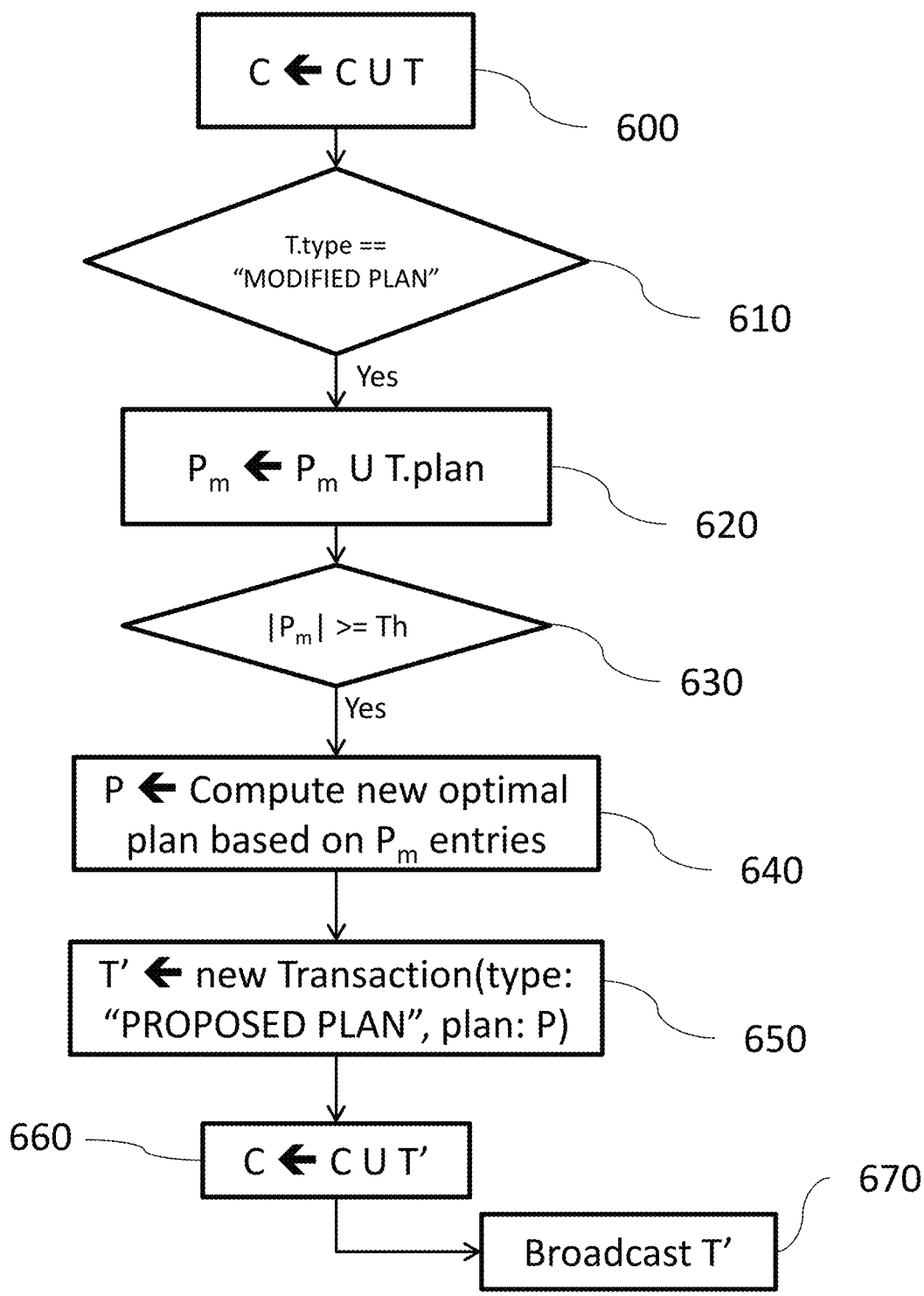

With reference to FIGS. 4, 5, and 6, there are provided schematics for sample algorithm steps involved in processing a new medication regime, adding transactions to a list of transactions, and creating a new optimal medication regime according to an embodiment of the invention. A new medication plan (also referred to herein as an initial healthcare regime) is generated (400) and stored in the blockchain (action not shown), and represented by variable P. Subsequently, a proposed plan (e.g., a proposed modified healthcare regime) that is related to P is generated (410), and represented by variable T. The blockchain is a chain of transactions and is represented by variable C. Thus, T is added ((420), (500), and (600)) to the blockchain (shown as the operation C union T, which is then stored in C). The system then broadcasts (430) T so that it can be added to the blockchain maintained in each node of the system. Similarly, another modified proposed regime/plan, represented by T', can be generated by an authorized healthcare worker, added (540) to the blockchain, and broadcast (550) to all nodes in the blockchain. In embodiments, particularly as shown in FIG. 6, a modified and optimal plan, represented by $P_m$, can be generated after a threshold (Th) of proposed plans/tokens T are received. An optimal plan T' is determined (640), stored in the blockchain (660), and broadcast to the nodes on the system (670).

Figure 7:
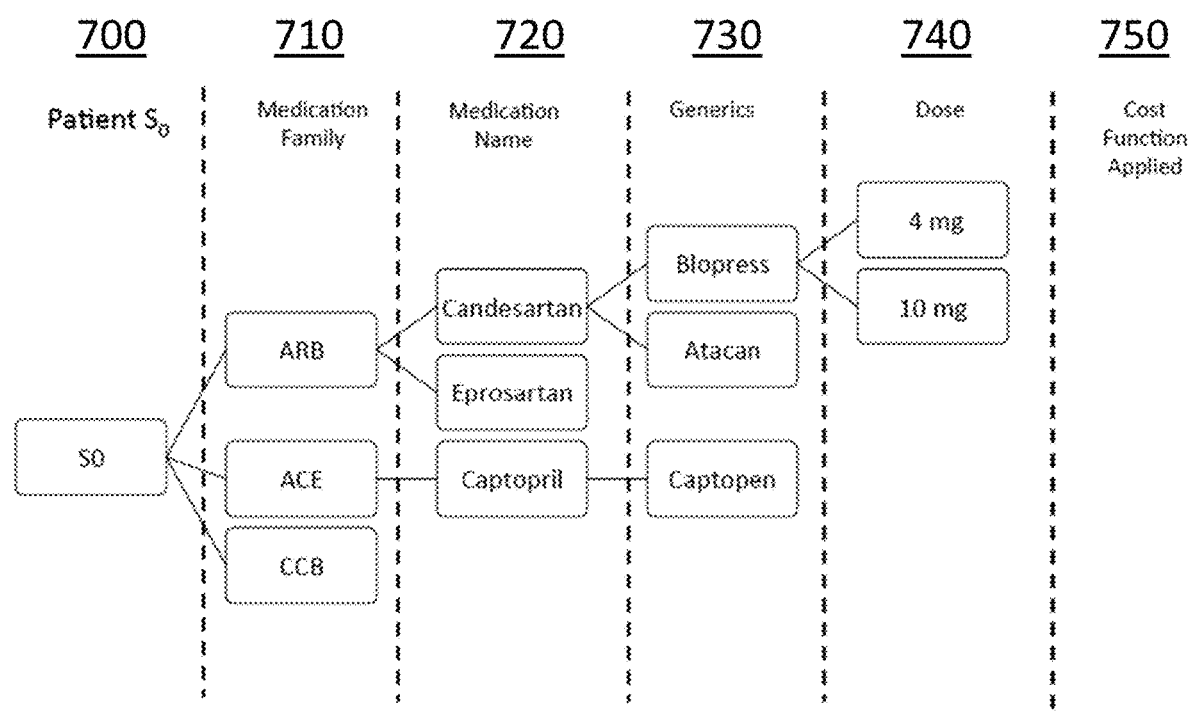
FIG. 7 provides a sample search hierarchy according to an embodiment of the invention.

With reference to FIG. 7 there is shown a sample search hierarchy according to an embodiment of the invention. The search hierarchy can take a breadth-first or a depth-first approach, as desired or appropriate. Each level may have a single option or several options, as shown. Patient level 700 shows, for example, a single option Patient $S_0$. Medication family level 710, in contrast, shows three options ARB, ACE, and CCB, representing different medication family options available to Patient $S_0$. The consensus algorithm can use tables such as the table shown in FIG. 7 to, for example, determine aspects of the a preference factor for a proposed modified healthcare regime (e.g., by determining whether the regime is consistent with known data/information, etc.).

Figure 8:
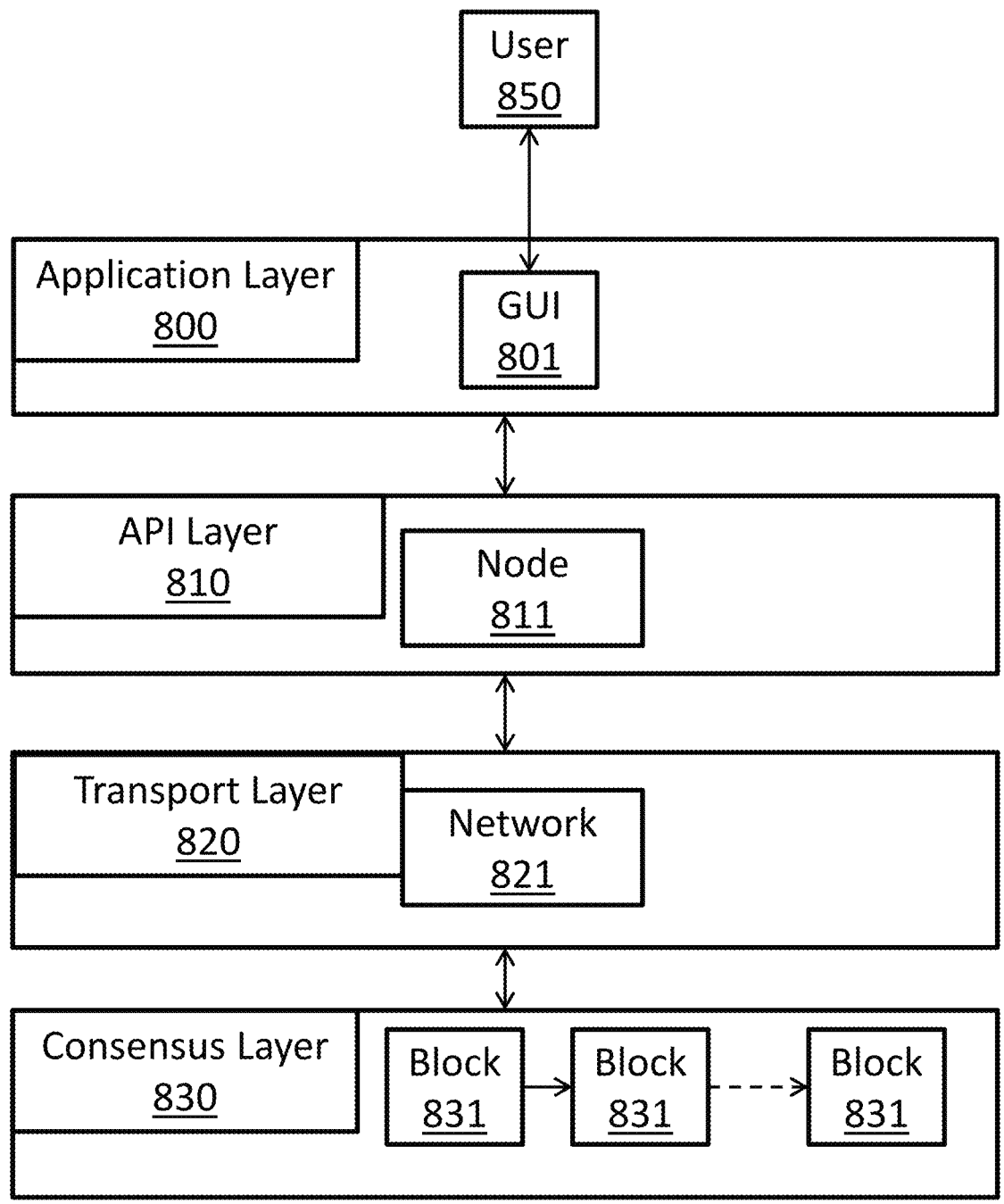
FIG. 8 provides a sample architecture of a blockchain implementation, including various layers of the system, according to an embodiment of the invention.

An example architecture is provided in FIG. 8, which shows application layer 800, API layer 810, transport layer 820, and consensus layer 830. Within application layer 800 is an application providing a user interface, specifically GUI 801, that provides an interface with user 850. Application layer 800 then communicates with the host node 811 upon which the application is running. Transport layer 820 then uses infrastructure such as network 821 to communicate between nodes participating in the blockchain. The blockchain data comprises a plurality of blocks 831, which reside in the consensus layer 830 resident on each node.

Throughout this disclosure, use of the term "server" is meant to include any computer system containing a processor and memory, and capable of containing or accessing computer instructions suitable for instructing the processor to carry out any desired steps. The server may be a traditional server, a desktop computer, a laptop, or in some cases and where appropriate, a tablet or mobile phone. The server may also be a virtual server, wherein the processor and memory are cloud-based.

The methods and devices described herein include a memory coupled to the processor. Herein, the memory is a computer-readable non-transitory storage medium or media, which may include one or more semiconductor-based or other integrated circuits (ICs) (such, as for example, field-programmable gate arrays (FPGAs) or application-specific ICs (ASICs)), hard disk drives (HDDs), hybrid hard drives (HHDs), optical discs, optical disc drives (ODDs), magneto-optical discs, magneto-optical drives, floppy diskettes, floppy disk drives (FDDs), magnetic tapes, solid-state drives (SSDs), RAM-drives, SECURE DIGITAL cards or drives, any other suitable computer-readable non-transitory storage media, or any suitable combination of two or more of these, where appropriate. A computer-readable non-transitory storage medium may be volatile, non-volatile, or a combination of volatile and non-volatile, where appropriate.

Throughout this disclosure, use of the term "or" is inclusive and not exclusive, unless otherwise indicated expressly or by context. Therefore, herein, "A or B" means "A, B, or both," unless expressly indicated otherwise or indicated otherwise by context. Moreover, "and" is both joint and several, unless otherwise indicated expressly or by context. Therefore, herein, "A and B" means "A and B, jointly or severally," unless expressly indicated otherwise or indicated otherwise by context.

It is to be understood that while the invention has been described in conjunction with examples of specific embodiments thereof, that the foregoing description and the examples that follow are intended to illustrate and not limit the scope of the invention. It will be understood by those skilled in the art that various changes may be made and equivalents may be substituted without departing from the scope of the invention, and further that other aspects, advantages and modifications will be apparent to those skilled in the art to which the invention pertains. The pertinent parts of all publications mentioned herein are incorporated by reference. All combinations of the embodiments described herein are intended to be part of the invention, as if such combinations had been laboriously set forth in this disclosure.

EXAMPLES

Example 1

FIGS. 4-6 show an example process involving validator nodes and voter nodes. In FIG. 4, given a new medication regime P, a new transaction T is added to the chain of transactions C. The proposed regimes may be evaluated and/or modified as shown in the figures. In the figures, the following variables are used:
C=Chain of transactions
T=Transaction
P=Medication Regime
$P_{m,i}$=Modified Regime by agent i
Th=Threshold, minimum number of required voters
P'=New Regime
T'=New Transaction
U=(Union function)

Example 2

In one implementation, agent attributes are assigned and used for role-based access granted to requests on the blockchain. Thus, each agent node (e.g., health workers, etc.) is assigned a set of attributes. These, for example, can be arranged as a JSON object (e.g., with binary and text fields such as: Agent ID; Verified Agent; Human Agent; Diabetes expertise and performance; Hypertension expertise and performance; etc.). The attributes are used to enable role-based access for agents to a request. Once an agent is given access to the request they can choose to examine the case notes and provide their expert opinion. In one case the role-based access is determined through preferences set by the requestor, although the preferences may be set by other users or admin.

Example 3

In an example, an initially proposed regime is shown in the Table below. Several modified medications (Med 1, etc.) for the initially proposed regime are also shown, and for each proposed med, the table provides input variables about the med. The table also shows, for each proposed med, the proposing health worker's consensus on the diagnosis. The input variables may be weighted by a variety of factors, such as known statistical/clinical results of the med against the proposed diagnosis, patient compliance predictions, potential drug interactions, cost, or the like. The input variables or the proposed modified medication regimes may also be weighted based on the expertise and experience of the health worker responsible for proposing the modified medication regime.

|  | Diagnosis | Family | Drug | Dose | Admin |
|---|---|---|---|---|---|
| Initially Proposed Regime | Hypertension | ACE | Captopril | 50 mg | Oral |
| Med 1 | Agree | ACE | Captopril | 30 mg | Oral |
| Med 2 | Agree | ARB | Eprosartan | 8 mg | Oral |
| Med 3 | Disagree | ARB | Candesartan | 12 mg | Injectable |
| Med 4 | Agree | ACE | Capoten | 30 mg | Oral |

For example, injectable drugs such as Med 3 are less likely to result in patient compliance and therefore a weighting factor is applied against Med 3. Also for example, a generic drug such as Capoten may be less expensive but otherwise identical compared with the brand name drug Captopril, and so may receive a positive weighting factor in the calculations for determining a modified medication regime. Also for example, the drug family may be ranked as highly important or of primary importance and therefore given the highest weight. In an example method, the algorithm for determining a modified regime involves minimizing a cost function involving the number of agents (doctors, guidelines, etc.), a distance function, and a penalty function, wherein the distance function is determined for each medical worker and their proposed regime relative to the initially proposed regime, and wherein the penalty function is determined based on a hierarchy of factors in the regime.

Example 4

FIG. 7 shows a search space for a proposed regime, including different variables for a medication, dosages, etc. The system/method can employ an algorithm involving a depth first or a breadth first search, as desired. The system/method can control the search and computation, for example, by searching for consensus on one or a few most important variable(s), and test for convergence i.e. restrict search depth by hierarchy.

What is claimed is:
1. A method of optimizing a healthcare regime, the method comprising:
receiving, by a first user device of a plurality of computers on a network, one or more healthcare regime tokens corresponding to a first set of proposed healthcare actions, wherein the first set of proposed healthcare actions correspond to a healthcare user associated with a healthcare blockchain;
receiving, by the first user device, a first digital signature of a first authoring healthcare worker who performs the first set of proposed healthcare actions, the first digital signature confirming a validity of the one or more healthcare regime tokens;
generating, by the first user device, a first healthcare regime block comprising at least the first set of proposed healthcare actions, the first digital signature, and a hash of at least a portion of a block of the healthcare blockchain;
revising, by the first user device, the healthcare blockchain based on the generated first healthcare regime block;
transmitting, by the first user device, the revised healthcare blockchain to one or more computers of the plurality of computers on the network, wherein the one or more computers of the plurality of computers on the network are configured to determine acceptance of the first healthcare regime block and to append the first healthcare regime block to the healthcare blockchain of the healthcare user;

receiving, by a second user device of the plurality of computers on the network, a version of the revised healthcare blockchain;

receiving, by the second user device, one or more additional healthcare regime tokens corresponding to a second set of proposed modified healthcare actions, the second set of proposed modified healthcare actions corresponding to the healthcare user;

receiving, by the second user device, a second digital signature of a second authorized healthcare worker who performs the second set of proposed modified healthcare actions;

determining a preference factor for at least one of the proposed modified healthcare actions;

generating, by the second user device, a second healthcare regime block comprising at least the second set of proposed modified healthcare actions, the second digital signature of the authorized healthcare worker, and a hash of at least a portion of another block of the healthcare blockchain;

updating, by the second user device, the received version of the healthcare blockchain based on the generated second healthcare regime block;

transmitting, by the second user device, the updated healthcare blockchain to one or more other computers of the plurality of computers on the network, wherein the one or more other computers of the plurality of computers on the distributed network is configured to determine acceptance of the second healthcare regime block and to append the second healthcare regime block to the healthcare blockchain of the healthcare user; and automatically generating a message comprising a healthcare action based on the healthcare blockchain, and transmitting the message via the network to a user account associated with the authoring healthcare worker, wherein the message alters a user interface to display the healthcare action based on the healthcare blockchain.

2. The method of claim 1, wherein causing the healthcare blockchain to be updated with the healthcare regime block comprises transmitting via the network the healthcare regime block to the plurality of computers.

3. The method of claim 1, further comprising receiving a plurality of proposed additional modified healthcare tokens, the plurality of proposed additional modified healthcare tokens representing a plurality of proposed additional modified healthcare actions pertaining to the healthcare regime.

4. The method of claim 1, further comprising
receiving a plurality of proposed additional modified healthcare tokens, the plurality of proposed additional modified healthcare tokens representing a plurality of proposed additional modified healthcare actions pertaining to the healthcare regime;

calculating a plurality of additional modified healthcare regime blocks for the healthcare regime, one additional modified healthcare regime block for each of the plurality of proposed additional modified healthcare tokens received; and causing the healthcare blockchain to be updated with the plurality of additional modified healthcare regime blocks.

5. The method of claim 4, further comprising applying a consensus algorithm to select a most effective modified healthcare regime block from the plurality of modified healthcare regime blocks.

6. The method of claim 5, further comprising automatically generating a message comprising a prescription for a medication, the medication based on the selected most effective modified healthcare regime block, and transmitting the message to the user account associated with the authoring healthcare worker for approval by the authoring healthcare worker, wherein approval by the authoring healthcare worker automatically transmits the prescription to a prescription filling system.

7. The method of claim 5, further comprising automatically generating a message comprising a healthcare action based on the selected most effective modified healthcare regime block, and transmitting the message via the network to a patient account associated with the healthcare user.

8. The method of claim 1, further comprising obtaining a consensus token indicative of an optimization of the healthcare actions and based on the one or more healthcare regime tokens.

9. The method of claim 1, wherein the preference factor comprises an experience factor, the experience factor calculated as a function of at least one of the following parameters: an experience of the authorized healthcare worker, an area of expertise of the authorized healthcare worker, and a success rate of the authorized healthcare worker.

10. The method of claim 1, wherein the preference factor comprises a compliance factor calculated from aggregated historical patient compliance data pertaining to at least one of the proposed modified healthcare actions.

11. The method of claim 1, wherein the preference factor comprises aggregated historical patient efficacy data pertaining to the at least one proposed modified healthcare actions.

12. The method of claim 1, wherein the healthcare blockchain further comprises a public key associated with the authoring healthcare worker, the public key operative to enable each device of the plurality of computers to check an authenticity of the healthcare regime block.

13. The method of claim 1, wherein the healthcare blockchain further comprises a public key associated with the authorized healthcare worker, the public key operative to enable each device of the plurality of computers to check an authenticity of the modified healthcare regime block.

14. The method of claim 1, wherein causing the healthcare blockchain to be updated with the healthcare regime block comprises transmitting via the network the healthcare regime block to the plurality of computers, and wherein the plurality of computers are suitable for use by a plurality of authorized healthcare workers.

15. The method of claim 1, wherein the generated message comprising a healthcare action is automatically transmitted to the user account associated with the authoring healthcare worker upon generation of a threshold of modified healthcare regime blocks within the healthcare blockchain.

16. The method of claim 1, wherein the altering of the user interface to display the healthcare action occurs automatically when a user device associated with the authoring healthcare worker receives the generated message comprising the healthcare action, and wherein the altering includes one or more actions automatically implemented, the one or more actions selected from: display of a visual alert in a GUI; production of an audible alert; modification of a screen view in a GUI; modification of a menu in a GUI; and modification of text in a healthcare user file.

17. A method for maintaining healthcare records, the method comprising:

maintaining a secure chain of healthcare blocks at each of a plurality of given computing nodes, wherein each given computing node is part of a set of computing nodes in a distributed network of computing nodes, wherein each of the set of computing nodes maintains the secure chain of healthcare blocks, wherein the secure chain of healthcare blocks maintained at each computing node comprises one or more healthcare blocks that respectively represent one or more healthcare actions associated with a healthcare user, and wherein at least one of the healthcare blocks in the secure chain of healthcare blocks represents at least one healthcare action generated by a first user device based on an authoring healthcare worker associated with the healthcare user, the authoring healthcare worker having an ability to prescribe a healthcare regime, at least one of the healthcare blocks in the secure chain of healthcare blocks being generated by the first user device based on a digital signature of the authoring healthcare worker;

adding, by a second user device, at least one healthcare block to the secure chain of healthcare blocks maintained at one of the given computing nodes based on a digital signature of an authorized healthcare worker and in response to receiving a proposed modified healthcare action;

determining a preference factor for the proposed modified healthcare action, wherein the preference factor is based on an experience factor personalized to the authorized healthcare worker, a compliance factor calculated from aggregated historical patient compliance data pertaining to a set of healthcare tokens, aggregated historical patient efficacy data, and a comparison factor;

transmitting a message comprising the preference factor and the proposed modified healthcare action to a user account associated with the authoring healthcare worker;

wherein the maintaining, adding, and determining steps are implemented via at least one processor operatively coupled to a memory associated with each of the given computing nodes.

18. The method of claim 17, wherein the message is configured to alter a user interface to automatically display the proposed modified healthcare action.

* * * * *